United States Patent [19]

Madding

[11] Patent Number: 4,596,884

[45] Date of Patent: Jun. 24, 1986

[54] 4-(2-PHENOXYETHYL)-1,2,4-TRIAZOLONE PROCESS INTERMEDIATES

[75] Inventor: Gary D. Madding, Evansville, Ind.

[73] Assignee: Bristol-Myers Company, New York, N.Y.

[21] Appl. No.: 740,594

[22] Filed: Jun. 3, 1985

Related U.S. Application Data

[62] Division of Ser. No. 556,727, Nov. 30, 1983.

[51] Int. Cl.$^4$ .......................................... C07C 125/067
[52] U.S. Cl. ...................................... 560/29; 548/263
[58] Field of Search .......................................... 560/29

[56] References Cited

U.S. PATENT DOCUMENTS 4,318,731  3/1982  Kajioka et al. .................. 560/29 X
4,487,773  12/1984  Temple et al. .................. 544/295 X

OTHER PUBLICATIONS

Dow Technical Bulletin, "Developmental 2-Ethyl-2-Oxazoline XAS-1454, Ethyloxazoline: An Intermediate for Aminoethylation".

W. Reid and Z. Czack, *Ann.*, 676, pp. 121–129 (1964).

M. Pesson, et al., *Bull Soc. Chim.*, Fr., pp. 1367–1371 (1962).

*Primary Examiner*—Bernard Helfin
*Attorney, Agent, or Firm*—Richard P. Ryan; Robert H. Uloth

[57] ABSTRACT

An improved process for the preparation of 5-ethyl-4-(2-phenoxyethyl)-1,2,4-triazolone, a useful intermediate in the synthesis of antidepressant 1,2,4-triazolones typified by 2-[3-[4-(3-chlorophenyl)-1-piperazinyl]propyl]-5-ethyl-4-(2-phenoxethyl)-2H-1,2,4-triazol-3(4H)-one, also known as nefazodone. The improved process is shorter and higher in yield than the former process, and the starting materials are cheap and readily available.

2 Claims, No Drawings

4-(2-PHENOXYETHYL)-1,2,4-TRIAZOLONE PROCESS INTERMEDIATES

This is a divisional application of application Ser. No. 556,727 filed 11/30/83.

BACKGROUND OF THE INVENTION

This invention describes an improved, more economical process for the synthesis of a valuable chemical intermediate (I)

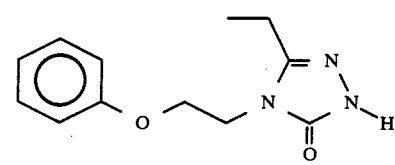

used in the manufacture of the antidepressant agent 2[3-[4-(3-chlorophenyl)-1-piperazinyl]propyl]-5-ethyl-4-(2-phenoxyethyl)-2H-1,2,4-triazol-3(4H)-one which is also known as nefazodone.

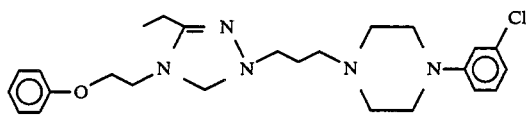

nefazodone

This subject intermediate, 5-ethyl-4-(2-phenoxyethyl)-1,2,4-triazolone, of Formula I is also known as MJ 14814 and its current synthesis, disclosed in pending application Ser. No. 509,266 and now U.S. Pat. No. 4,487,773 as Example 5, is shown in Scheme 1. An overall yield of 33% for Scheme 1 is predicted from yield calculations of the individual steps in Example 5 of the pending application.

Scheme 1

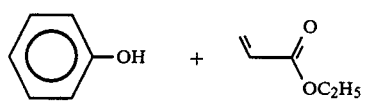

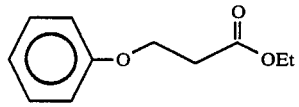

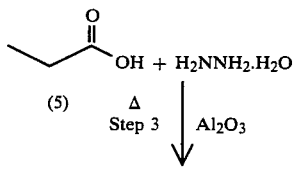

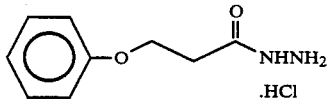

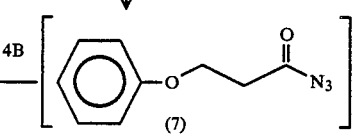

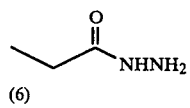

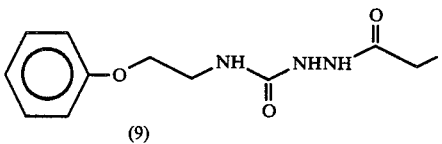

As can be seen in Scheme 1, the preparation of MJ 14814 starts with phenol and ethyl acrylate, an obnoxious material with a high vapor pressure. This process has been successfully scaled up and used repeatedly giving MJ 14814 in 25–30% overall yield from phenol.

MJ 14814 is converted to the antidepressant agent nefazodone (MJ 13754) as disclosed in the above cited pending application. This conversion involves reaction of MJ 14814 with 1-(3-chlorophenyl)-4-(3-chloropropyl)piperazine hydrochloride (10)

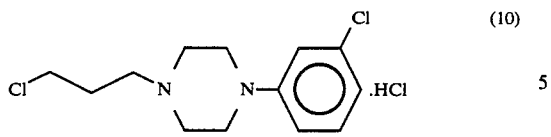

(10)

Preparation of MJ 14814 via Scheme 1 involves six steps and four isolated intermediates, two of which are liquids requiring purification by vacuum distillation. By contrast, the improved process described hereinafter is comprised of four steps involving only three isolated intermediates, all of which are solids, with an overall yield of MJ 14814 of 40–55% from phenol. In comparison, the prior art method, represented by Scheme I, is a longer process requiring more labor and providing MJ 14814 in much lower yield.

The following references relate to component steps of the instant process described herein.

1. Dow Technical Bulletin, "Developmental 2-Ethyl-2-Oxazoline XAS-1454 Ethyloxazoline: An Intermediate for Aminoethylation." This reference describes the synthesis of N-(2-phenoxyethyl)propionamide, an intermediate compound of the instant process.

2. W. Reid and A. Czack, Ann. 676, pp. 121–129 (1964). This reference teaches the reaction of imidoyl ethers with ethyl carbazate to give amidrazones which then cyclize on further heating to 1,2,4-triazoles as outlined below in Scheme 2.

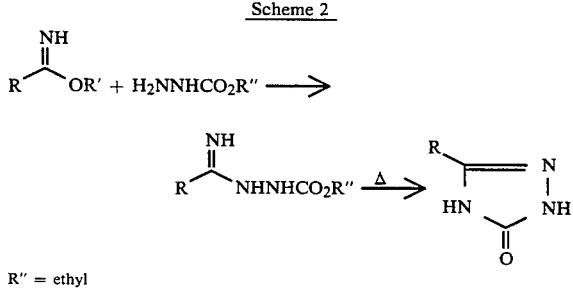

R" = ethyl

However, there is no disclosure of the use of N-substituted imidoyl ethers which would be necessary to obtain a desired N-substituted triazolone. 3. M. Pesson, et al., *Bull. Soc. Chim.*, Fr., pp. 1367–71 (1962). This reference reports a very low yield synthesis (0.3%) of a triazolone with the desired substitution pattern via the process shown below in Scheme 3.

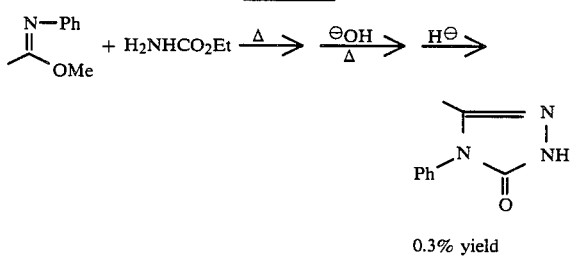

0.3% yield

The authors state that imidoyl ethers of secondary amides are difficult to make (p. 1364, bottom second column). Pesson, et al., do disclose preparation of a triazolone with the desired substitution pattern but via a synthesis, shown as Scheme 4, which is different from that in the instant process. The reference synthesis begins with an imidoyl ether of a primary amide to give an intermediate carbethoxy hydrazone which is then reacted with a primary amine.

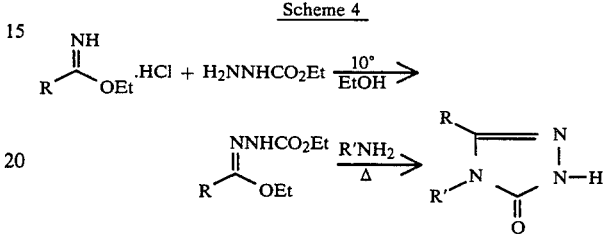

Note that the carbazate displaces the imine function in Scheme 4 representing another feature distinguishing from the process of the instant invention.

Pesson, et al., also disclose that thioamides are more reactive than amides, giving N-substituted amidrazones on reaction with carbazate. However, when the N-substituent is alkyl, as required in the instant process, no reaction with ethyl carbazate was observed. Finally, Pesson, et al., teach activation of a thiobenzamide with dimethylsulfate followed by reaction with carbazate to give the triazolone product. Again, there is no disclosure involving activation of alkyl carboxylic acid thioamides, a structural prerequisite for the instant process.

In summary, references 2 and 3 essentially describe reactions of certain amide derivatives with carbazate esters to eventually yield triazolone products but with distinguishing variations in structural relationship to the product produced by the instant process.

SUMMARY OF THE INVENTION

This invention relates to an improved synthetic process which can be adapted for large-scale preparation of the useful chemical intermediate, 5-ethyl-4-(2-phenoxyethyl)-1,2,4-triazolone. The instant process starts from phenol and 2-ethyl-2-oxazoline, raw materials which are cheap and readily available. The subject improved process offers advantages in economies of both material and labor costs by virtue of being shorter in length, involving fewer intermediate isolations, and providing a higher yield of product.

DETAILED DESCRIPTION OF THE INVENTION

The following flow chart, Scheme 5, illustrates the preparation of MJ 14814 from readily available starting materials utilizing the instant process.

Scheme 5

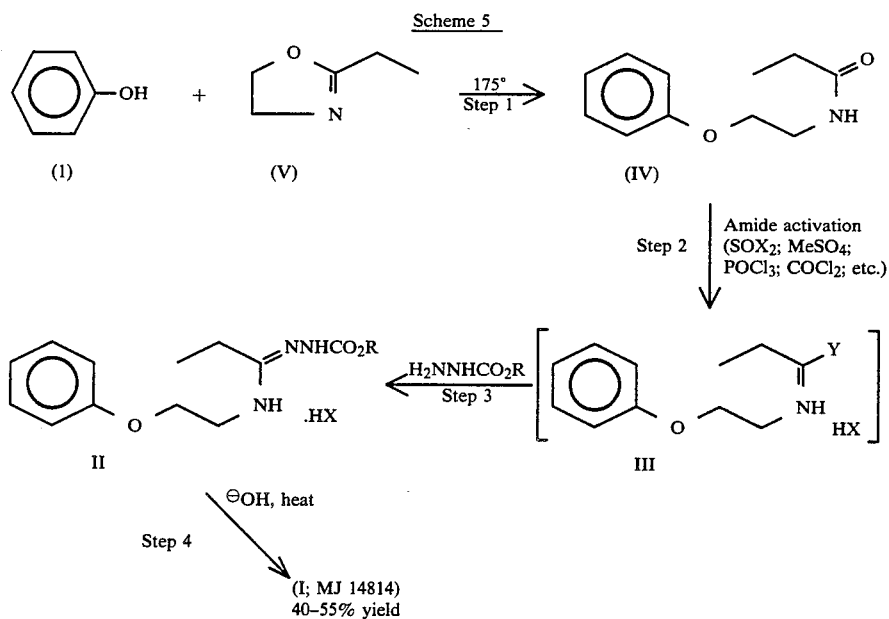

(I; MJ 14814)
40–55% yield

In Scheme 5, R is $C_{1-4}$ alkyl; X is Cl, Br, or $SO_4$; Y is Cl, Br, or OR; and amide activation is formation of a reactive imidoyl halide or ester by treatment of the amide with a suitable activating reagent such as $SOCl_2$, $SOBr_2$, $POCl_3$, dimethyl sulfate, phosgene, etc.

Step 1 of the scheme outlined above involves the reaction of phenol (1) and 2-ethyl-2-oxazoline (V) to give the intermediate compound N-(2-phenoxyethyl)-propionamide (IV). The starting materials for step 1 are commercially available. Step 2, activation of the amide (IV), is accomplished by treatment of IV with an amide-activating reagent such as thionyl chloride, thionyl bromide, phosphorus oxychloride, phosgene, dimethy sulfate, and the like, to give an imidoyl halide or ester intermediate (III). The preferred agents are phosgene or phosphorus oxychloride. Intermediate III is not isolated but is allowed to react with an alkyl carbazate of formula $H_2NNHCO_2R$, R=methyl is preferred, in step 3 to give the novel triazolone precursor (II). In step 4 the hydrazinecarboxylate acid addition salt (II) is converted to its base form and cyclized to the desired triazolone product (1) by heating.

This four-step improved process involves isolation of only two intermediate products (IV and II) in addition to the target compound, I. By way of comparison, the current process involves six steps and the isolation of four intermediates, two of which are liquid and require purification by vacuum distillation. The reduced handling of intermediates in the instant process significantly reduces labor costs in manufacture.

The synthesis of MJ 14814 as represented in the improved process is preferably carried out as a series of four steps going from the simplest starting materials (phenol, 2-ethyloxazoline) to MJ 14814. The steps comprising the process are as follows:

(1) Adding 2-ethyl-2-oxazoline to hot (150°) phenol and maintaining heating at about 175° for 16 additional hours. The oil is then quenched in water to give N-(2-phenoxyethyl)propionamide (IV) in approximately 90% yield.

(2) Adding phosgene or phosphorus oxychloride to a solution of IV containing a catalytic amount of imidazole in methylene chloride to give a solution of the intermediate imidoyl chloride hydrochloride (III).

(3) Treating the solution of III with a solution of an alkyl carbazate to give alkyl [1-[(2-phenoxyethyl)amino]propylidene]-hydrazine carboxylate hydrochloride (II) is about 75% yield.

(4) The free base form of II, resulting from the treatment of II with a basifying agent, is heated in solution for several hours to yield I in about 75%.

DESCRIPTION OF SPECIFIC EMBODIMENTS

The process of this invention is illustrated in greater detail by the following examples directed to preferred embodiments of the hereinafter described process steps. These examples, however, should not be construed as limiting the scope of the present invention in any way. In examples which follow, used to illustrate the foregoing processes, temperatures are expressed, as in the foregoing, in degrees centigrade (°). Melting points are uncorrected. The nuclear magnetic resonance (NMR) spectral characteristics refer to chemical shifts ($\delta$) expressed as parts per million (ppm) versus tetramethylsilane (TMS) as reference standard. The relative area reported for the various shifts in the H NMR spectral data corresponds to the number of hydrogen atoms of a particular functional type in the molecule. The nature of the shifts as to multiplicity is reported as broad singlet (bs), singlet (s), doublet (d), triplet (t), quartet (q), or multiplet (m). Abbreviations employed are DMSO-$d_6$ (deuterodimethylsulfoxide), CDCl$_3$ (deuterochloroform), and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight.

EXAMPLE 1

Methyl Carbazate

An alternate name for this commercially available chemical is methyl hydrazinocarboxylate. Methyl carbazate may also be synthesized by adding 85% hydrazine hydrate (58.5 g, 1.00 mole) with stirring to dimethyl carbonate (90.0 g, 1.00 mole) over a 10 min period. The mixture quickly warmed to 64° and became clear. The solution was stirred for another 15 min and the volatile materials were stripped in vacuo at 70°. Upon cooling, the residue solidified. It was collected on a filter and after drying in air gave 69.3 g (76.9%) of white solid, m.p. 69.5°–71.5°.

EXAMPLE 2

N-(2-Phenoxyethyl)propionamide (IV)

Phenol (13.1 moles) was heated to 150° and stirred under $N_2$ as 2-ethyl-2-oxazoline (12.2 moles) was added over 1 hr. The mixture was heated to 175±3°. After heating 16 hr the oil was cooled to about 140°, and then it was poured into water (12 L) with vigorous stirring. The mixture was stirred and cooled, and at about 25° the mixture was seeded with crystalline amide product. The material solidified and the supernatant was decanted. The residual solid was stirred with 17 L of hot (85°) water. The mixture was cooled to 25°, seeded with the amide product, and the mixture refrigerated. The resulting granular solid was collected on a filter, rinsed with several portions of water and left to air dry. This gave a 92% yield of material, m.p. 61.5°–64°.

EXAMPLE 3

A. Methyl [1-[(2-Phenoxyethyl]amino]propylidene Hydrazinecarboxylate Hydrochloride (II)

Phosgene (57.4 g, 0.58 mole) was added to a solution of N-(2-phenoxyethyl)propionamide (IV, 112.0 g, 0.58 mole) and imidazole (0.4 g, 0.006 mole) in 450 mL methylene chloride over 1 hr employing cooling so that the temperature did not exceed 25°. The reaction solution was then stirred at 25° for an additional 2.5 hr. A solution of methyl carbazate (52.5 g, 0.58 mole) in 500 mL methylene chloride was stirred over 25 g of a molecular sieve for 15 min and then the solution was filtered. The filtrate was added under $N_2$ over a 0.5 hr period to the amide/phosgene solution while employing cooling 15°–20°. A voluminous precipitate formed and the mixture was left to stir at 25° under $N_2$. After stirring for a total of 16 hrs, the mixture was filtered to isolate a solid. The solid was stirred in 750 mL methylene chloride for 15 min, refiltered, and then dried in vacuo at 65° for 2 hrs to give 135 g (77%) white solid, m.p. 150°–154°. Recrystallization of the product from isopropanol gives analytically pure material, m.p. 157°–159°.

Anal. Calcd. for $C_{13}H_{19}N_3O_3 \cdot HCl$: C, 51.74; H, 6.68; N, 13.92; Cl, 11.75. Found: C, 51.73; H, 6.76; N, 13.94; Cl, 11.78.

NMR (DMSO-$d_6$): 1.15 (3,t [7.5 Hz]); 1.28 (3,t [7.5 Hz]); 2.74 (2,m); 3.66 (3,s); 3.70 (3,s); 3.81 (2,m); 4.19 (2,m); 6.98 (3,m); 7.31 (2,m); 9.67 (3,bt [6.8 Hz]); 10.04 (3,bs); 10.40 (3,bs); 10.90 (3,bs); 11.72 (3,bs).

IR (KBr): 695, 755, 1250, 1270, 1500, 1585, 1600, 1670, 1745, and 2900 cm$^{-1}$.

By appropriate modification of the above procedure (A), thionyl chloride, thionyl bromide, dimethyl sulfate or other amideactivating agents may be employed in place of phosgene. A slightly different procedure (B) may also be used.

B. Methyl [1-[(2-Phenoxyethyl]amino]propylidene Hydrazinecarboxylate (II Base Form)

Phosphorus oxychloride (53.0 g, 0.346 mole) was slowly added to a solution of N-(2-phenoxyethyl)propionamide (IV, 100.0 g, 0.518 mole) in 200 mL methylene chloride while being stirred under nitrogen. This solution was stirred for 4 hrs at which time a solution (dried over moecular sieve 4A) of methyl carbazate (46.4 g, 0.518 mole) in 600 mL methylene chloride was added to the stirring solution over a 0.5 hr period. The resulting mixture was stirred and heated at gentle reflux under nitrogen for 18 hr. The mixture was then stirred with 1.0 L ice-water. The layers were separated and the aqueous layers extracted with an additional 200 mL methylene chloride. The aqueous layer was made basic (pH 12) with aqueous sodium hydroxide. This resulted in precipitation of the free base form of II which was collected by filtration, rinsed with water and dried in air to give 65.8 g of product, m.p. 97°–99°.

Anal. Calcd. for $C_{13}H_{19}N_3O_3$: C, 58.85; H, 7.22; N, 15.84. Found: C, 59.02; H, 7.24; N, 15.92.

When this free base form of II is employed for the conversion to I, the preliminary basification step outlined in Example 4 (which follows) is skipped. The base form of II is cyclized directly by gently refluxing in xylene according to the procedure of Example 4.

EXAMPLE 4

5-Ethyl-4-(2-phenoxyethyl)-2H-1,2,4-triazol-3(4H)-one (I)

Methyl [1-[(2-phenoxyethyl)amino]propylidene]hydrazine carboxylate hydrochloride (II, 655.3 g, 2.17 mole) was stirred vigorously with 4.0 L methylene chloride, 2.4 L water and 179.4 g 50% NaOH (2.24 moles). The layers were separated and the organic layer was dried ($K_2CO_3$) and concentrated in vacuo. The residue as stirred in 1.2 L xylene at gentle reflux for 2.5 hrs and then the solution was refrigerated. The solid was collected on a filter, rinsed with toluene and left to air dry. The white crystalline solid weighed 89.5 g (76.9%), m.p. 134.5°–138°.

Additional purification may be accomplished in the following manner. A portion of I (171.2 g, 0.73 mole) was dissolved in a boiling solution of 41.0 g (0.73 mole) KOH in 3.0 L water. The solution was treated with Celite filter-aid and activated charcoal and filtered. The filtrate was stirred in an ice bath, and 37% HCl (61.0 mL, 0.73 mole) was added. The solid was collected on a filter, rinsed with water and air dried to give 166.0 g (97% recovery) of fine white cyrstalline product, m.p. 137.5°–138°.

What is claimed is:

1. The compound methyl [1-[(2-phenoxyethyl)amino]propylidene]hydrazine carboxylate or an acid addition salt thereof.

2. The compound methyl [1-[(2-phenoxyethyl)amino]propylidene]hydrazine carboxylate hydrochloride.

* * * * *